United States Patent [19]

Harmon

[11] 4,129,902

[45] Dec. 19, 1978

[54] ELBOW PROSTHESIS

[76] Inventor: Stanley D. Harmon, 10511 Royal Oak Rd., Oakland, Calif. 94605

[21] Appl. No.: 814,362

[22] Filed: Jul. 11, 1977

[51] Int. Cl.² .............................................. A61F 1/24
[52] U.S. Cl. ........................................ 3/1.91; 128/92 C
[58] Field of Search ................................ 3/1.9–1.911; 128/92 C

[56] References Cited

U.S. PATENT DOCUMENTS

| | | | |
|---|---|---|---|
| 3,816,854 | 6/1974 | Schlein | 3/1.91 |
| 3,852,831 | 12/1974 | Dee | 3/1.91 |
| 3,919,725 | 11/1975 | Swanson et al. | 3/1.91 |
| 3,990,117 | 11/1976 | Pritchard et al. | 3/1.91 |
| 3,990,118 | 11/1976 | Strickland et al. | 3/1.91 |
| 4,057,858 | 11/1977 | Helfet | 3/1.91 |

FOREIGN PATENT DOCUMENTS 2248820  5/1975  France ........................................ 3/1.91

Primary Examiner—Ronald L. Frinks
Attorney, Agent, or Firm—R. S. Sciascia; Charles D. B. Curry; Francis I. Gray

[57] ABSTRACT

A total elbow prosthesis employing three separate parts, each separately and firmly attached to the humerus, ulna and radius, respectively, which articulate together to provide for triangular support and bracing as in a natural elbow joint.

4 Claims, 4 Drawing Figures

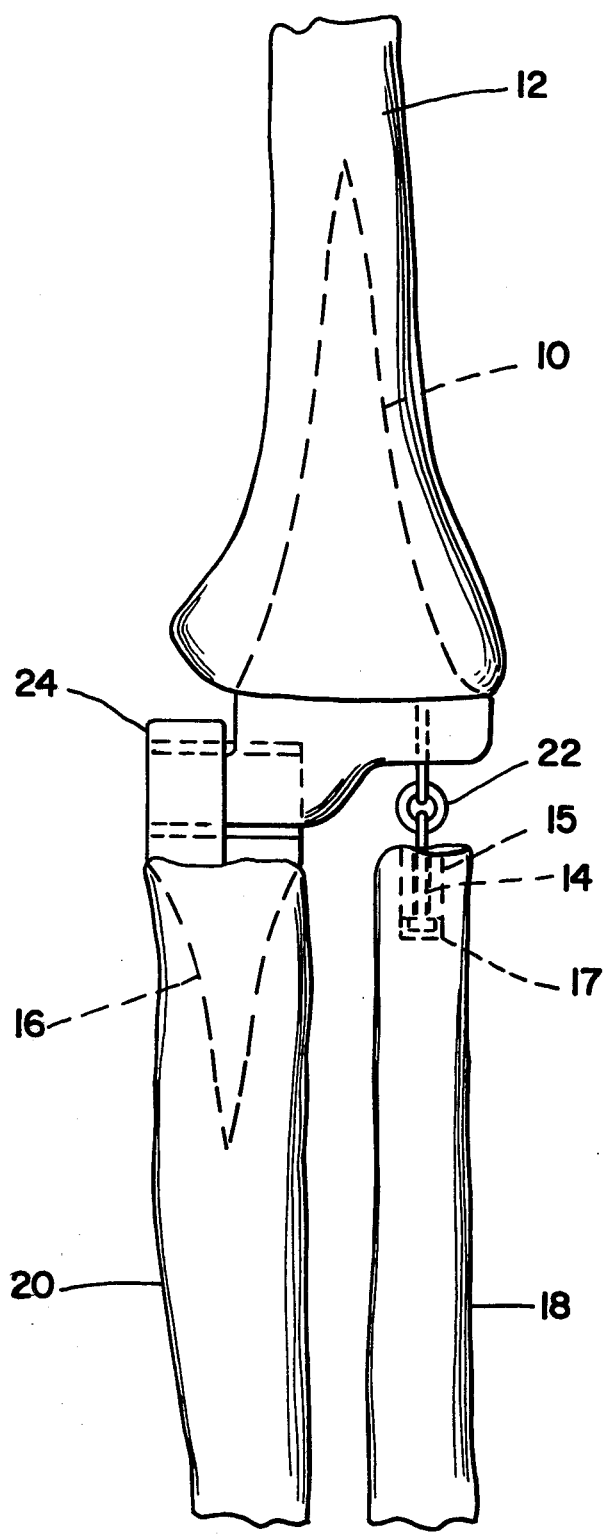
FIG_1

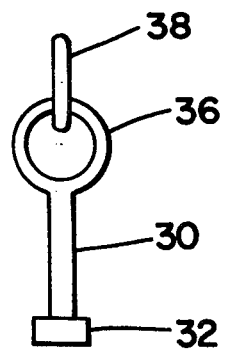
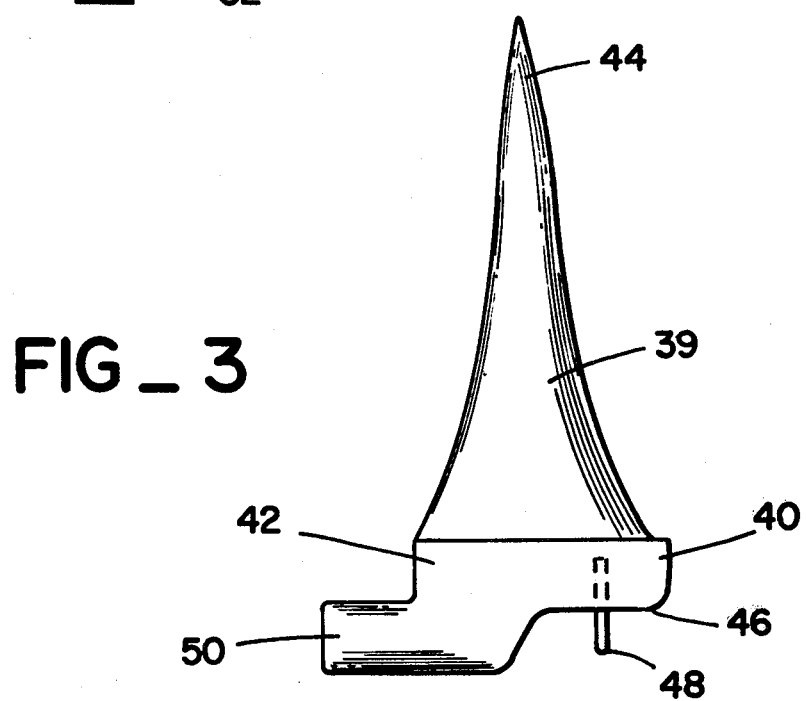
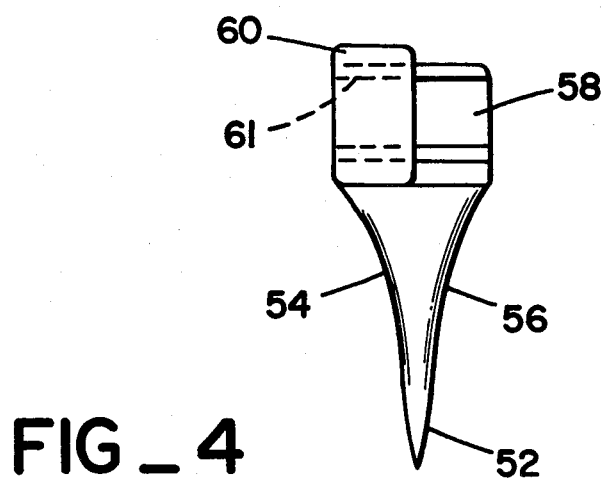

ELBOW PROSTHESIS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

1. Field of the Invention

The present invention relates to human prosthetics, and more particularly to elbow prosthetics.

2. Description of the Prior Art

Solutions to surgical removal of the elbow joint are of basically two kinds: (1) amputation with subsequent fitting of an artificial arm, and (2) a surgically implanted joint. Prior elbow prostheses are notable for their lack of stability. Only the humeral-ulnar articulation is used for elbow stability and function, ignoring the humeral-radial articulation entirely.

SUMMARY OF THE INVENTION

Accordingly, the present invention provides a total elbow prosthesis having three parts which are each separately and firmly attached to the humerus, ulna and radius, respectively. The parts are interconnected with each other to articulate together, providing for triangular support and bracing as in a natural elbow joint. The humeral implant interlocks with the ulnar implant axially to assure stability. The humeral-radial articulation between the humeral implant and the radial implant employs a three-link chain swivel arangement to allow pronation-supination of the forearm. Thus, the total elbow prosthesis uses both sides of the joint to provide stability through the triangulation of forces as in a natural elbow joint.

STATEMENTS OF THE OBJECTS OF THE INVENTION

Therefore, it is an object of the present invention to provide a total elbow prosthesis.

Another object of the present invention is to provide an elbow prosthesis which assures anterior and posterior stability.

A further object of the present invention is to provide an elbow prosthesis which allows for full pronation and supination of the forearm while allowing for normal flexion and extension.

Yet another object of the present invention is to provide an elbow prosthesis which assures elbow stability in the varus and valgus directions.

Other objects, advantages and novel features of the invention will become apparent from the following detailed description of the invention when considered in conjunction with the accompanying drawing.

BRIEF DESCRIPTION OF THE DRAWING

FIG. 1 is a perspective view of an elbow prosthesis according to the present invention.

FIG. 2 is a perspective view of the radial implant of the elbow prosthesis.

FIG. 3 is a perspective view of the humeral implant of the elbow prosthesis.

FIG. 4 is a perspective view of the ulnar implant of the elbow prosthesis.

DESCRIPTION OF THE PREFERRED EMBODIMENT

Referring now to FIG. 1 a humeral implant 10 is shown firmly attached to the humerus 12 by means well known to orthopedic practitioners. Likewise, ulnar implant 16 is shown firmly attached to the ulna 20. A radial implant 14 is shown attached to the radius 18 inside a sleeve 15 of ultra-high molecular weight polyethylene, the sleeve being firmly attached as a lining to a cavity 17 in the radius. The radial implant 14 rotates freely within the sleeve 15. The humeral implant 10 is connected to the radial implant 14 by a three-link chain 22, while it interlocks axially with the ulnar implant 16 by a simple shaft and bearing joint 24.

The radial implant 14, as shown in FIG. 2, has a stem 30 of chromecobalt alloy with a tip 32 at one end and radial link 36 at the other end which is one of the members of the three-link chain 22. The tip 32 prevents the radial implant from being removed from the sleeve 15 once the radial implant is set in the radius 18. Through the radial link 36 is freely joined a middle link 38 of the three-link chain 22.

FIG. 3 shows the humeral implant 10 which has a body 39. The body 39 is shaped similar to the humerus, forming a tip 44 at one end. A radial segment 40 terminates in a flat face 46 to which is affixed a humeral link 48, the third link of the three-link chain 22. An ulnar segment 42 terminates in a shaft 50 which is parallel to the flat face 46 of the radial segment 40 and approximately perpendicular to the long axis of the humeral implant 10.

The ulnar implant 16, shown in FIG. 4, also has a tip 52 and a body which has a medial side 54 and a lateral side 56 tapered to approximately conform to the shape of the ulna. The end of the ulnar implant 16 opposite the tip 52 has a bearing surface 58 which is conformed to provide the shaft and bearing joint 24 when interlocked with the humeral shaft 50. The end of the bearing 58 on the medial side 54 forms a ring 60 which completely encloses the humeral shaft 50 when the humeral implant 10 and the ulnar implant 16 are interlocked. A bearing 61 of ultra-high molecular weight polyethylene inside ring 60 and on the bearing surface 58 provide for smooth sliding between the elements of the shaft and bearing joint 24.

Stem implantation may be used to achieve stability of the implants in all three bones, while acrylic filler is used for locking the prosthesis into the bone. The olecranon-trochlea joint is replaced by the simple shaft and bearing joint 24, thereby providing anterior and posterior stability which allows a full normal range of elbow motion in flexion and extension. The capitular-radial head articlulation is replaced by the three-link chaim 22 allowing for full pronation and supination of the forearm while providing for normal flexion and extension. The links prevent any significant displacement with anterior and posterior forces, while they provide the third side of the triangle assuring elbow stability in a varus and valgus direction. The implants may be made of plastic and copper-chromium alloy.

Thus, the present invention provides a total elbow prosthesis by making use of the radius to provide for triangular support and bracing as in a normal elbow joint.

What is claimed is:

1. An elbow prosthesis comprising:

(a) a humeral implant having a radial and an ulnar segment at one end contiguous to each other, said ulnar segment having a shaft extending medially;
(b) a radial implant;
(c) an ulnar implant having a bearing surface which interlocks with said shaft of said humeral implant to form a shaft and bearing joint; and
(d) a three-link chain which connects said radial segment of said humeral implant with said radial implant.

2. An elbow prosthesis as recited in claim 1 wherein said radial implant comprises:
(a) a stem;
(b) a sleeve around said stem which allows said stem to rotate freely within said sleeve;
(c) a tip integral to one end of said stem of a larger diameter than said stem so that said tip cannot pass through said sleeve; and
(d) a radial link integral to the other end of said stem which forms one link of said three-link chain.

3. An elbow prosthesis as recited in claim 2 further comprising a lining on said bearing surface which reduces friction between said shaft and said bearing surface.

4. An elbow prosthesis as recited in claim 3 wherein said three-link chain comprises:
(a) said radial link of said radial implant;
(b) a humeral link firmly attached to said radial segment of said humeral implant; and
(c) a middle link which freely connects said radial link to said humeral link.

* * * * *